(12) United States Patent
Higuchi et al.

(10) Patent No.: US 11,727,806 B2
(45) Date of Patent: Aug. 15, 2023

(54) IDENTIFYING A PARKING SPOT BASED ON CONGESTION-DEPENDENT PARKING NAVIGATION PREFERENCES

(71) Applicant: Toyota Motor Engineering & Manufacturing North America, Inc., Plano, TX (US)

(72) Inventors: Takamasa Higuchi, Mountain View, CA (US); Kentaro Oguchi, Mountain View, CA (US)

( * ) Notice: Subject to any disclaimer, the term of this patent is extended or adjusted under 35 U.S.C. 154(b) by 134 days.

(21) Appl. No.: 17/477,176

(22) Filed: Sep. 16, 2021

(65) Prior Publication Data

US 2023/0085360 A1    Mar. 16, 2023

(51) Int. Cl.
*G08G 1/14* (2006.01)
*G08G 1/01* (2006.01)
*G06N 20/00* (2019.01)
*B60W 30/06* (2006.01)

(52) U.S. Cl.
CPC .......... *G08G 1/146* (2013.01); *B60W 30/06* (2013.01); *G06N 20/00* (2019.01); *G08G 1/0129* (2013.01); *G08G 1/144* (2013.01)

(58) Field of Classification Search
CPC ...... G08G 1/146; G08G 1/0129; G08G 1/144; B60W 30/06; G06N 20/00
See application file for complete search history.

(56) References Cited

U.S. PATENT DOCUMENTS

| | | | |
|---|---|---|---|
| 9,747,797 B1* | 8/2017 | Ghosh | G08G 1/005 |
| 9,805,602 B2* | 10/2017 | Tobolski | G08G 1/144 |
| 10,832,575 B2 | 11/2020 | Khoo et al. | |
| 11,526,798 B2* | 12/2022 | Pinel | G08G 1/14 |
| 2012/0062395 A1* | 3/2012 | Sonnabend | G08G 1/0112 340/932.2 |
| 2013/0257632 A1* | 10/2013 | Harber | G08G 1/144 340/932.2 |
| 2014/0214319 A1 | 7/2014 | Vucetic et al. | |

(Continued)

FOREIGN PATENT DOCUMENTS

| | | |
|---|---|---|
| CN | 107680401 | 2/2018 |
| CN | 109326139 | 2/2019 |

(Continued)

OTHER PUBLICATIONS

Shin, Jong-Ho et al., "A Dynamic Information-Based Parking Guidance for Megacities considering Both Public and Private Parking," Journal of Advances Transportation, 2017, 19 pages.

(Continued)

*Primary Examiner* — Ryan W Sherwin
(74) *Attorney, Agent, or Firm* — Burbage Law, P.C.; Jon-Michael Burbage

(57) ABSTRACT

The disclosure describes a method for an ego vehicle. The method includes determining that a vehicle needs to park. The method further includes identifying a parking facility within proximity to the vehicle and a corresponding congestion level of the parking facility. The method further includes selecting a first parking model from two or more parking models based on the corresponding congestion level being closer to a first congestion range than a second congestion range. The method further includes identifying a parking spot for the vehicle within the parking facility based on the first parking model.

20 Claims, 6 Drawing Sheets

(56) References Cited

U.S. PATENT DOCUMENTS

| | | | |
|---|---|---|---|
| 2014/0313058 A1* | 10/2014 | Chen | G08G 1/0116 |
| | | | 340/932.2 |
| 2016/0055749 A1 | 2/2016 | Nicoll et al. | |
| 2016/0117925 A1 | 4/2016 | Akavaram et al. | |
| 2016/0247326 A1 | 8/2016 | de Souza et al. | |
| 2018/0218605 A1* | 8/2018 | Mowatt | G08G 1/144 |
| 2018/0313661 A1* | 11/2018 | Eyster | G08G 1/144 |
| 2018/0335777 A1* | 11/2018 | Gibbs | G05D 1/0297 |
| 2020/0160712 A1* | 5/2020 | Beaurepaire | G08G 1/148 |
| 2020/0258386 A1* | 8/2020 | Lu | G08G 1/148 |
| 2020/0320877 A1* | 10/2020 | Dagley | G08G 1/205 |
| 2020/0355515 A1* | 11/2020 | Saxena | G06V 20/176 |
| 2021/0019671 A1* | 1/2021 | Cao | G06Q 30/0283 |
| 2021/0074157 A1* | 3/2021 | Boutcher-West | G08G 1/143 |
| 2021/0125498 A1* | 4/2021 | Munger | H04W 4/023 |
| 2021/0134155 A1* | 5/2021 | Bravi | G06N 20/00 |
| 2021/0223054 A1 | 7/2021 | Fuchs | |
| 2021/0241621 A1* | 8/2021 | Higuchi | G01C 21/3694 |
| 2021/0253132 A1* | 8/2021 | Coimbra de Andrade | |
| | | | G05D 1/0278 |
| 2021/0280062 A1* | 9/2021 | Baird | G06N 20/00 |
| 2021/0295066 A1* | 9/2021 | Vallance | G06T 7/74 |
| 2021/0295697 A1* | 9/2021 | Vallance | G06N 20/00 |

FOREIGN PATENT DOCUMENTS

| | | |
|---|---|---|
| CN | 112819226 | 5/2021 |
| WO | 2014117016 | 7/2014 |

OTHER PUBLICATIONS

Takayama, Yuki et al., "Scheduling preferences, parking competition, and bottleneck congestion: a model of trip timing and parking location choices by heterogeneous commuters," Jan. 10, 2016, 34 pages.

Geng, Yanfeng et al., "New 'smart parking' System Based on Resource Allocation and Reservations," IEEE Transactions on Intelligent Transportation Systems, vol. 14, No. 3, Sep. 2013, pp. 1129-1139.

Higuchi, Takamasa et al., "A Collaborative Approach to Finding Available Parking Spots," in Proceedings of the 2019 90th IEEE Vehicular Technology Conference (VTC2019-Fall), 2019, 5 pages.

Higuchi, Takamasa et al., "Monitoring Live Parking Availability by Vision-based Vehicular Crowdsensing," in Proceedings of 2020 IEEE Global Communications Conference (GLOBECOM), 2020, pp. 1-5.

Elsonbaty, Amira A. et al., "The smart parking management system," International Journal of Computer Science & Information Technology, vol. 12, No. 4, Aug. 2020, 12 pages.

Hess, Stephane et al., "An analysis of parking behaviour using discrete choice models calibrated on SP datasets," 44th Congress of the European Regional Science Association: "Regions and Fiscal Federalism," Aug. 2004, 30 pages.

Lefkowitz, Melanie, "Smart parking software could ease congestion, save time," retrieved from Internet at https://news.cornell.edu/stories/2020/06/smart-parking-software-could-ease-congestion-save-time, Jun. 8, 2020, 2 pages.

* cited by examiner

IDENTIFYING A PARKING SPOT BASED ON CONGESTION-DEPENDENT PARKING NAVIGATION PREFERENCES

BACKGROUND

The specification relates to identifying a parking spot based on a parking model that corresponds to a congestion level.

Vehicle drivers and autonomous vehicles struggle to locate parking spots for vehicles, which causes wasted time and stress. Existing solutions attempt to locate parking spots for vehicles. A problem with these existing solutions, however, is that they are overly simplistic and fail to accurately predict a driver's preferences, thereby degrading the user experience.

In addition, existing solutions fail to provide enough information for a driver to locate the available parking spot. This is difficult logistically because the driver tries to use a display with information about the parking spot to find the physical location of the parking spot. This also presents a safety problem because if the driver is too focused on a display, the driver may get into more vehicular accidents.

SUMMARY

Described are embodiments of a method for an ego vehicle. The method includes determining that a vehicle needs to park. The method further includes identifying a parking facility within proximity to the vehicle and a corresponding congestion level of the parking facility. The method further includes selecting a first parking model from two or more parking models based on the corresponding congestion level being closer to a first congestion range than a second congestion range. The method further includes identifying a parking spot for the vehicle within the parking facility based on the first parking model.

Implementations may include one or more of the following features. The method may further include recording historical search paths that describe how the vehicle travelled to park in selected spots and locations of other available parking spots in the parking facilities and the corresponding congestion levels associated with the parking facilities and generating the two or more parking models based on the historical search paths, wherein the first parking model is associated with the first congestion range and a second parking model is associated with the second congestion range. In some embodiments, identifying the parking spot for the vehicle within the parking facility includes: receiving an identification of candidate parking spots that are available within the parking facility, where the candidate parking spots are identified based on onboard sensors of vehicles travelling within the parking facility, scoring the candidate parking spots within the parking facility based on the first parking model, wherein the first parking model uses parking attributes to score the candidate parking spots, and generating a recommendation for the parking spot along a parking search path based on the parking spot having a best ranking. In some embodiments, scoring the candidate parking spots includes calculating a per-criterion score for each candidate parking spot along a candidate search path and the corresponding congestion levels are defined as a ratio of available parking spots to occupied parking spots. In some embodiments, the two or more parking models are generated by a machine-learning model and training data for the machine-learning model includes historical search paths for a set of vehicles. The method may further include providing a recommendation to a user of the vehicle with the parking spot, receiving a selection from the user of the parking spot that was identified, and instructing an autonomous vehicle system of the vehicle to automatically park in the parking spot. The method may further include providing a recommendation to a user of the vehicle with the parking spot, determining that the user rejected the recommendation of the parking spot, and updating the first parking model based on the user rejecting the recommendation. The method may further include displaying a recommendation for the parking spot within a user interface, wherein the recommendation includes a search path to reach the parking spot. In some embodiments, determining that the vehicle needs to park is based on identifying a navigation trip and wherein identifying the parking facility within proximity to the vehicle includes identifying the parking facility within proximity to the vehicle at an end of the navigation trip.

One general aspect includes a system for an ego vehicle, comprising: a processor; and a non-transitory memory storing computer code which, when executed by the processor, causes the processor to: determine that a vehicle needs to park, identify a parking facility within proximity to the vehicle and a corresponding congestion level of the parking facility, select a first parking model from two or more parking models based on the corresponding congestion level being closer to a first congestion range than a second congestion range, and identify a parking spot for the vehicle within the parking facility based on the first parking model.

Implementations may include one or more of the following features. The system where the computer code, when executed by the processor, further causes the processor to: record historical search paths that describe how the vehicle travelled to park in selected spots and locations of other available parking spots in the parking facilities and the corresponding congestion levels associated with the parking facilities and generate the two or more parking models based on the historical search paths, wherein the first parking model is associated with the first congestion range and a second parking model is associated with the second congestion range. In some embodiments, identifying the parking spot for the vehicle within the parking facility includes: receiving an identification of candidate parking spots that are available within the parking facility, where the candidate parking spots are identified based on onboard sensors of vehicles travelling within the parking facility, scoring the candidate parking spots within the parking facility based on the first parking model, wherein the first parking model uses parking attributes to score the candidate parking spots, and generating a recommendation for the parking spot along a parking search path based on the parking spot having a best ranking. In some embodiments, scoring the candidate parking spots includes calculating a per-criterion score for each candidate parking spot along a candidate search path and the corresponding congestion levels are defined as a ratio of available parking spots to occupied parking spots. In some embodiments, the two or more parking models are generated by a machine-learning model and training data for the machine-learning model includes historical search paths for a set of vehicles.

One general aspect includes a computer program product comprising a non-transitory memory storing computer-executable code that, when executed by a processor, causes the processor to: determine that a vehicle needs to park, identify a parking facility within proximity to the vehicle and a corresponding congestion level of the parking facility, select a first parking model from two or more parking models based on the corresponding congestion level being closer to a first congestion range than a second congestion range, and identify a parking spot for the vehicle within the parking facility based on the first parking model.

Implementations may include one or more of the following features. The computer program product, where the computer-executable code further causes the processor to: record historical search paths that describe how the vehicle travelled to park in selected spots and locations of other available parking spots in the parking facilities and the corresponding congestion levels associated with the parking facilities and generate the two or more parking models based on the historical search paths, wherein the first parking model is associated with the first congestion range and a second parking model is associated with the second congestion range. In some embodiments, identifying the parking spot for the vehicle within the parking facility includes: receiving an identification of candidate parking spots that are available within the parking facility, where the candidate parking spots are identified based on onboard sensors of vehicles travelling within the parking facility, scoring the candidate parking spots within the parking facility based on the first parking model, wherein the first parking model uses parking attributes to score the candidate parking spots, and generating a recommendation for the parking spot along a parking search path based on the parking spot having a best ranking. In some embodiments, scoring the candidate parking spots includes calculating a per-criterion score for each candidate parking spot along a candidate search path and the corresponding congestion levels are defined as a ratio of available parking spots to occupied parking spots. In some embodiments, the two or more parking models are generated by a machine-learning model and training data for the machine-learning model includes historical search paths for a set of vehicles. In some embodiments, identifying the parking spot for the vehicle within the parking facility includes: providing a recommendation to a user of the vehicle with the parking spot, receiving a selection from the user of the parking spot that was identified, and instructing an autonomous vehicle system of the vehicle to automatically park in the parking spot.

At least one improvement of the parking application described herein over the existing solutions includes that it determines that a driver's preferences may change depending on the current congestion level of a parking facility. The parking application determines a first parking model based on a congestion level of a parking facility being closing to a first congestion range than a second congestion range. The parking application identifies a parking spot for the vehicle within the parking facility based on the first parking model. The existing systems do not use different parking models based on a level of congestion. In embodiments where the vehicle includes the autonomous driving system, the autonomous driving system may automatically park in the available parking spot.

Another improvement of the parking application described herein is that for embodiments where a driver drives the vehicle, the parking application generates a user interface that helps navigate the driver to the available parking spot. The user interface helps reduce confusion and improves the safety of the vehicle.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

Example Overview

Figure 1:
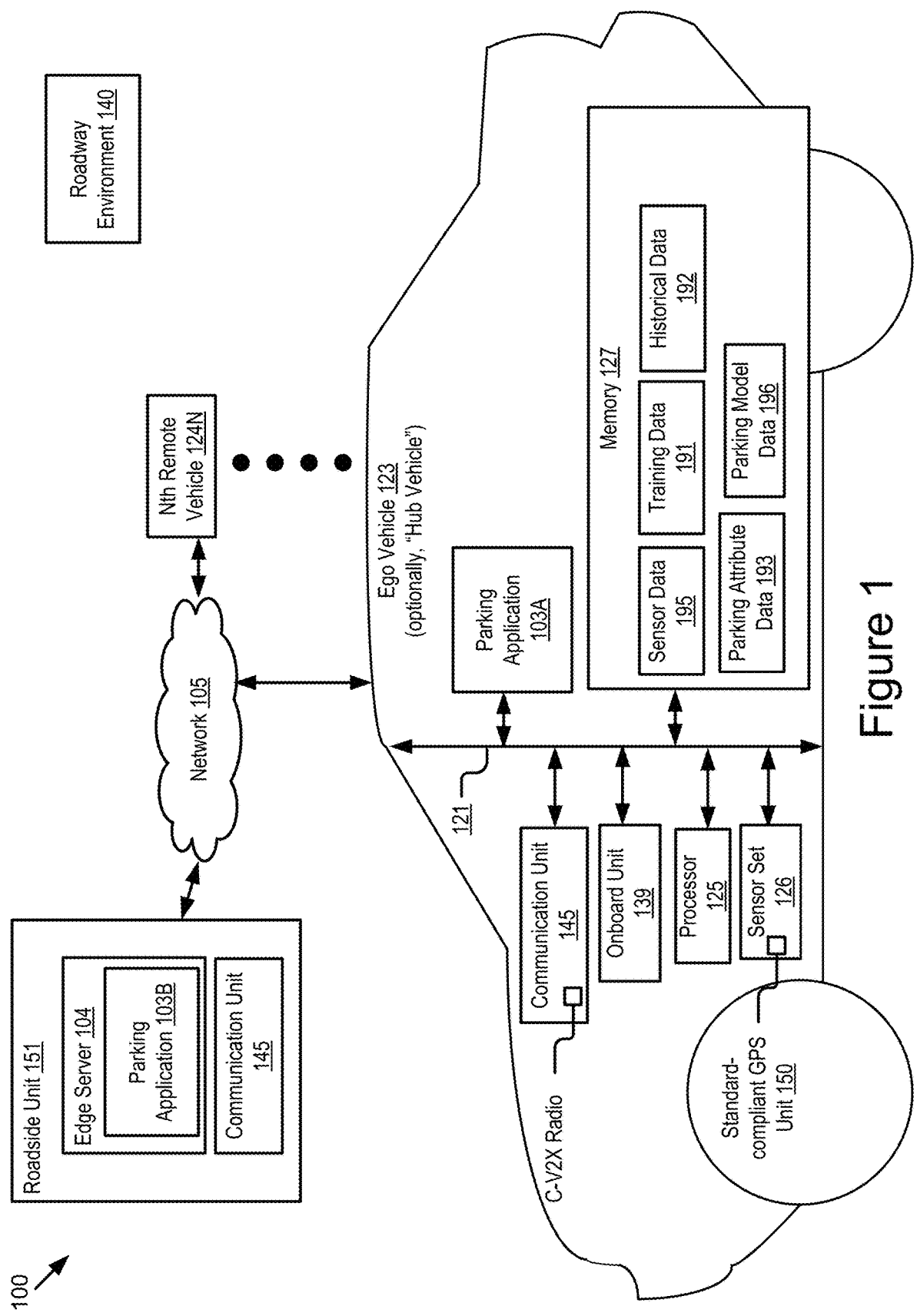
FIG. 1 is a block diagram illustrating an example operating environment for a parking application according to some embodiments.

In some embodiments, an ego vehicle includes a parking application that records historical search paths that describe how the vehicle travelled to park in selected spots and locations of other available parking spots in parking facilities and corresponding congestion levels associated with the parking facilities. For example, the congestion levels are defined as a ratio of available parking spots to the occupied parking spots in a parking facility. The parking application generates two or more parking models based on the historical search paths, where a first parking model is associated with a first congestion range and a second parking model is associated with a second congestion range. In some embodiments, the two or more parking models are machine-learning models.

The parking application determines that a vehicle needs to park, for example, because the parking application identifies a navigation trip associated with navigation software, the vehicle is travelling at a time and direction that correspond to a historical trip taken by the vehicle, etc. The parking application identifies a parking facility within proximity to the vehicle and a corresponding congestion level of the parking facility. For example, the parking application determines that parking facilities exist within proximity to an end of the navigation trip or an end of the historical trip taken by the vehicle.

The parking application selects a first parking model from the two or more parking models based on the corresponding congestion level of the parking facility being closer to the first congestion range than the second congestion range. The parking application identifies a parking spot for the vehicle within the parking facility based on the first parking model. In some embodiments, the parking application generates a recommendation to a user of the vehicle with the parking spot. In one example, the user may select the parking spot and the parking application instructs an autonomous vehicle system of the vehicle to automatically park in the parking spot. In another example, the user rejects the recommendation of the parking spot and the parking application updates the first parking model based on the user rejecting the recommendation.

In some embodiments, a parking application that is part of the ego vehicle transmits the historical search paths to a parking application that is part of an edge server (e.g., that is part of a roadside unit (RSU)), which generates the parking models. The parking application on the ego vehicle may transmit the historical search paths via vehicle-to-everything (V2X) communications. As described herein, examples of V2X communications include, but are not limited to, one or more of the following: Dedicated Short Range Communication (DSRC) (including BSMs and Personal Safety Messages (PSMs), among other types of DSRC communication); Long-Term Evolution (LTE); millimeter wave (mmWave) communication; 3G; 4G; 5G; LTE-V2X; 5G-V2X; LTE-Vehicle-to-Vehicle (LTE-V2V); LTE-Device-to-Device (LTE-D2D); Voice over LTE (VoLTE); etc. In some examples, the V2X communications can include V2V communications, Vehicle-to-Infrastructure (V2I) communications, Vehicle-to-Network (V2N) communications or any combination thereof.

Examples of a V2X message described herein include, but are not limited to, the following messages: a Dedicated Short Range Communication (DSRC) message; a Basic Safety Message (BSM); a Long-Term Evolution (LTE) message; a LTE-V2X message (e.g., a LTE-Vehicle-to-Vehicle (LTE-V2V) message, a LTE-Vehicle-to-Infrastructure (LTE-V2I) message, an LTE-V2N message, etc.); a 5G-V2X message; and a millimeter wave message, etc.

In some embodiments, a connected vehicle that includes the parking application is a DSRC-equipped vehicle. A DSRC-equipped vehicle is a vehicle which: (1) includes a DSRC radio; (2) includes a DSRC-compliant GPS unit; and (3) is operable to lawfully send and receive DSRC messages in a jurisdiction where the DSRC-equipped vehicle is located. A DSRC radio is hardware that includes a DSRC receiver and a DSRC transmitter. The DSRC radio is operable to wirelessly send and receive DSRC messages. DSRC has a range of substantially 500 meters and is designed to be compatible for wirelessly sending and receiving messages among mobile nodes such as vehicles and RSUs. A DSRC-compliant GPS unit is operable to provide positional information for a vehicle (or some other DSRC-equipped device that includes the DSRC-compliant GPS unit) that has lane-level accuracy.

As used herein, the words "geographic location," "location," "geographic position" and "position" refer to a latitude and longitude of an object (or, a latitude, longitude, and elevation of an object) such as the vehicle. The example embodiments described herein provide positioning information that describes a geographic position of a vehicle with an accuracy of one or more of: (1) at least plus or minus 1.5 meters in relation to the actual geographic position of the vehicle in 2 dimensions including a latitude and a longitude; and (2) at least plus or minus 3 meters in relation to the actual geographic position of the vehicle in an elevation dimension. Accordingly, the example embodiments described herein are able to describe the geographic position of the vehicle with lane-level accuracy or better.

Example Operating Environment

Referring to FIG. 1, depicted is an operating environment 100 for a parking application 103 (here, parking application 103A and parking application 103B may be referred to collectively or individually as the "parking application 103" since, for example, the parking application 103A-103B are different instances of the parking application and may provide similar functionality).

The operating environment 100 may include one or more of the following elements: an ego vehicle 123 (referred to herein as a "vehicle 123" or an "ego vehicle 123"); an Nth remote vehicle 124 (where "N" refers to any positive whole number greater than one); and a roadside unit 151. These elements are communicatively coupled to one another via a network 105. These elements of the operating environment 100 are depicted by way of illustration. In practice, the operating environment 100 may include one or more of the elements depicted in FIG. 1. The Nth remote vehicle 124 may be referred to as a remote vehicle 124. As depicted, the roadside unit 151 includes an edge server 104.

In some embodiments, the ego vehicle 123, the remote vehicle 124, and the edge server 104 include similar elements. For example, each of these elements of the operating environment 100 include their own processor 125, bus 121, memory 127, communication unit 145, processor 125, sensor set 126, onboard unit 139 (not included in the edge server 104), standard-compliant GPS unit 150 (not included in the edge server 104), and parking application 103. These elements of the ego vehicle 123, the remote vehicle 124, and the edge server 104 provide the same or similar functionality regardless of whether they are included in the ego vehicle 123, the remote vehicle 124, or the edge server 104. Accordingly, the descriptions of these elements will not be repeated in this description for each of the ego vehicle 123, the remote vehicle 124, and the edge server 104.

In the depicted embodiment, the ego vehicle 123, the remote vehicle 124, and the edge server 104 store similar digital data.

The network 105 may be a conventional type, wired or wireless, and may have numerous different configurations including a star configuration, token ring configuration, or other configurations. Furthermore, the network 105 may include a local area network (LAN), a wide area network (WAN) (e.g., the Internet), or other interconnected data paths across which multiple devices and/or entities may communicate. In some embodiments, the network 105 may include a peer-to-peer network. The network 105 may also be coupled to or may include portions of a telecommunications network for sending data in a variety of different communication protocols. In some embodiments, the network 105 includes Bluetooth® communication networks or a cellular communications network for sending and receiving data including via short messaging service (SMS), multimedia messaging service (MMS), hypertext transfer protocol (HTTP), direct data connection, wireless application protocol (WAP), e-mail, DSRC, full-duplex wireless communication, mmWave, WiFi (infrastructure mode), WiFi (ad-hoc mode), visible light communication, TV white space communication and satellite communication. The network 105 may also include a mobile data network that may include 3G, 4G, 5G, LTE, LTE-V2X, LTE-D2D, VoLTE or any other mobile data network or combination of mobile data networks. Further, the network 105 may include one or more IEEE 802.11 wireless networks.

In some embodiments, the network 105 is a V2X network. For example, the network 105 must include a vehicle, such as the ego vehicle 123, as an originating endpoint for each wireless communication transmitted by the network 105. An originating endpoint is the endpoint that initiated a wireless communication using the network 105. In some embodiments, the network 105 is a vehicular network.

In some embodiments, the network 105 is a C-V2X network. In some embodiments, one or more of the ego vehicle 123 and the remote vehicle 124 are C-V2X equipped vehicles. For example, the ego vehicle 123 includes a standard-compliant GPS unit 150 that is an element of the sensor set 126 and a C-V2X radio that is an element of the communication unit 145. The network 105 may include a C-V2X communication channel shared among the ego vehicle 123 and a second vehicle such as the remote vehicle 124.

A C-V2X radio is hardware radio that includes a C-V2X receiver and a C-V2X transmitter. The C-V2X radio is operable to wirelessly send and receive C-V2X messages on a band that is reserved for C-V2X messages.

The ego vehicle 123 may include a car, a truck, a sports utility vehicle, a bus, a semi-truck, a drone, or any other roadway-based conveyance. In some embodiments, the ego vehicle 123 may include an autonomous vehicle or a semi-autonomous vehicle. Although not depicted in FIG. 1, in some embodiments, the ego vehicle 123 includes an autonomous driving system. The autonomous driving system includes code and routines that provide autonomous driving features to the ego vehicle 123 to render the ego vehicle 123 an autonomous vehicle or a highly autonomous vehicle. In some embodiments, the ego vehicle 123 is a Level III autonomous vehicle or higher as defined by the National Highway Traffic Safety Administration and the Society of Automotive Engineers.

The ego vehicle 123 is a connected vehicle. For example, the ego vehicle 123 is communicatively coupled to the network 105 and operable to send and receive messages via the network 105. For example, the ego vehicle 123 transmits and receives C-V2X messages via the network 105.

The ego vehicle 123 includes one or more of the following elements: a processor 125; a sensor set 126; a standard-compliant GPS unit 150; a communication unit 145; an onboard unit 139; a memory 127; and a parking application 103a. These elements may be communicatively coupled to one another via a bus 121. In some embodiments, the communication unit 145 includes a C-V2X radio.

The processor 125 includes an arithmetic logic unit, a microprocessor, a general-purpose controller, or some other processor array to perform computations and provide electronic display signals to a display device. The processor 125 processes data signals and may include various computing architectures including a complex instruction set computer (CISC) architecture, a reduced instruction set computer (RISC) architecture, or an architecture implementing a combination of instruction sets. Although FIG. 1 depicts a single processor 125 present in the ego vehicle 123, multiple processors may be included in the ego vehicle 123. The processor 125 may include a graphical processing unit. Other processors, operating systems, sensors, displays, and physical configurations may be possible.

In some embodiments, the processor 125 may be an element of a processor-based computing device of the ego vehicle 123. For example, the ego vehicle 123 may include one or more of the following processor-based computing devices and the processor 125 may be an element of one of these devices: an onboard vehicle computer; an electronic control unit; a navigation system; a vehicle control system (e.g., an advanced driver assistance system ("ADAS") or autonomous driving system); a head unit; or the onboard unit 139.

The onboard unit 139 is a special purpose processor-based computing device. In some embodiments, the onboard unit 139 is a communication device that includes one or more of the following elements: the communication unit 145; the processor 125; the memory 127; and the parking application 103a. In some embodiments, the onboard unit 139 is the computer system 200 depicted in FIG. 2. In some embodiments, the onboard unit 139 is an electronic control unit (ECU).

The sensor set 126 includes one or more onboard sensors. The sensor set 126 may record sensor measurements that describe the ego vehicle 123 or the physical environment that includes the ego vehicle 123. The sensor data includes digital data that describes the sensor measurements.

In some embodiments, the sensor set 126 may include one or more sensors that are operable to measure the physical environment outside of the ego vehicle 123. For example, the sensor set 126 may include cameras, lidar, radar, sonar and other sensors that record one or more physical characteristics of the physical environment that is proximate to the ego vehicle 123.

In some embodiments, the sensor set 126 may include one or more of the following sensors: an altimeter; a gyroscope; a proximity sensor; a microphone; a microphone array; an accelerometer; a camera (internal or external); a LIDAR sensor; a laser altimeter; a navigation sensor (e.g., a global positioning system sensor of the standard-compliant GPS unit 150); an infrared detector; a motion detector; a thermostat; a sound detector, a carbon monoxide sensor; a carbon dioxide sensor; an oxygen sensor; a mass air flow sensor; an engine coolant temperature sensor; a throttle position sensor; a crank shaft position sensor; an automobile engine sensor; a valve timer; an air-fuel ratio meter; a blind spot meter; a curb feeler; a defect detector; a Hall effect sensor, a manifold absolute pressure sensor; a parking sensor; a radar gun; a speedometer; a speed sensor; a tire-pressure monitoring sensor; a torque sensor; a transmission fluid temperature sensor; a turbine speed sensor (TSS); a variable reluctance sensor; a vehicle speed sensor (VSS); a water sensor; a wheel speed sensor; and any other type of automotive sensor.

The sensor set 126 is operable to record sensor data 195. The sensor data 195 includes digital data that describes images or other measurements of the physical environment such as the conditions, objects, and other vehicles present in the roadway environment. Examples of objects include parking facilities, parking spots that are occupied, parking spots that are unoccupied, pedestrians, animals, traffic signs, traffic lights, potholes, etc. Examples of conditions include weather conditions, road surface conditions, shadows, leaf cover on the road surface, and any other condition that is measurable by a sensor included in the sensor set 126.

The physical environment may include a roadway region, parking lot, or parking garage that is proximate to the ego vehicle 123. The sensor data may describe measurable aspects of the physical environment. In some embodiments, the physical environment is the roadway environment 140. As such, in some embodiments, the roadway environment 140 includes one or more of the following: a roadway region that is proximate to the ego vehicle 123; a parking lot that is proximate to the ego vehicle 123; a parking garage that is proximate to the ego vehicle 123; the conditions present in the physical environment proximate to the ego vehicle 123; the objects present in the physical environment proximate to the ego vehicle 123; and other vehicles present in the physical environment proximate to the ego vehicle 123; any other tangible object that is present in the real-world and proximate to the ego vehicle 123 or otherwise measurable by the sensors of the sensor set 126 or whose presence is determinable from the digital data stored on the memory 127. An item is "proximate to the ego vehicle 123" if it is directly measurable by a sensor of the ego vehicle 123 or its presence is inferable and/or determinable by the parking application 103 based on analysis of the sensor data that is recorded by the ego vehicle 123 and/or the roadside unit 151.

In some embodiments, the sensors of the sensor set 126 are operable to collect digital data that is stored as sensor data 195. The sensors of the sensor set 126 include any sensors that are necessary to measure and record the measurements described by the sensor data 195. In some embodiments, the sensor data 195 includes any sensor measurements that are necessary to generate the other digital data stored by the memory 127. In some embodiments, the sensor data 195 includes digital data that describes any sensor measurements that are necessary for the parking application 103.

The standard-compliant GPS unit 150 includes a GPS unit that is compliant with one or more standards that govern the transmission of V2X wireless communications ("V2X communication" if singular, "V2X communications" if plural). For example, some V2X standards require that BSMs are transmitted at intervals by vehicles and that these BSMs must include within their payload GPS data having one or more attributes.

An example of an attribute for GPS data is accuracy. In some embodiments, the standard-compliant GPS unit 150 is operable to generate GPS measurements which are sufficiently accurate to describe the location of the ego vehicle 123 with lane-level accuracy. Lane-level accuracy is necessary to comply with some of the existing and emerging standards for V2X communication (e.g., C-V2X communication). Lane-level accuracy means that the GPS measurements are sufficiently accurate to describe which lane of a roadway that the ego vehicle 123 is traveling (e.g., the geographic position described by the GPS measurement is accurate to within 1.5 meters of the actual position of the ego vehicle 123 in the real-world). Lane-level accuracy is described in more detail below.

In some embodiments, the standard-compliant GPS unit 150 is compliant with one or more standards governing V2X communications but does not provide GPS measurements that are lane-level accurate.

In some embodiments, the standard-compliant GPS unit 150 includes any hardware and software necessary to make the ego vehicle 123 or the standard-compliant GPS unit 150 compliant with one or more of the following standards governing V2X communications, including any derivative or fork thereof: EN 12253:2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); and EN 13372:2004 Dedicated Short-Range Communication (DSRC)—DSRC profiles for RTTT applications (review); EN ISO 14906:2004 Electronic Fee Collection—Application interface.

In some embodiments, the standard-compliant GPS unit 150 is operable to provide GPS data describing the location of the ego vehicle 123 with lane-level accuracy. For example, the ego vehicle 123 is traveling in a lane of a multi-lane roadway. Lane-level accuracy means that the lane of the ego vehicle 123 is described by the GPS data so accurately that a precise lane of travel of the ego vehicle 123 may be accurately determined based on the GPS data for this vehicle 123 as provided by the standard-compliant GPS unit 150.

An example process for generating GPS data describing a geographic location of an object (e.g., a queue, the ego vehicle 123, the remote vehicle 124, or some other object located in a roadway environment) is now described according to some embodiments. In some embodiments, the parking application 103 includes code and routines that are operable, when executed by the processor 125, to cause the processor to: analyze (1) GPS data describing the geographic location of the ego vehicle 123 and (2) sensor data describing the range separating the ego vehicle 123 from an object and a heading for this range; and determine, based on this analysis, GPS data describing the location of the object. The GPS data describing the location of the object may also have lane-level accuracy because, for example, it is generated using accurate GPS data of the ego vehicle 123 and accurate sensor data describing information about the object.

In some embodiments, the standard-compliant GPS unit 150 includes hardware that wirelessly communicates with a GPS satellite (or GPS server) to retrieve GPS data that describes the geographic location of the ego vehicle 123 with a precision that is compliant with a V2X standard. One example of a V2X standard is the DSRC standard. Other standards governing V2X communications are possible. The DSRC standard requires that GPS data be precise enough to infer if two vehicles (one of which is, for example, the ego vehicle 123) are located in adjacent lanes of travel on a roadway. In some embodiments, the standard-compliant GPS unit 150 is operable to identify, monitor and track its two-dimensional position within 1.5 meters of its actual position 68% of the time under an open sky. Since roadway lanes are typically no less than 3 meters wide, whenever the two-dimensional error of the GPS data is less than 1.5 meters the parking application 103 described herein may analyze the GPS data provided by the standard-compliant GPS unit 150 and determine what lane the ego vehicle 123 is traveling in based on the relative positions of two or more different vehicles (one of which is, for example, the ego vehicle 123) traveling on a roadway at the same time.

By comparison to the standard-compliant GPS unit 150, a conventional GPS unit which is not compliant with the DSRC standard is unable to determine the location of a vehicle (e.g., the ego vehicle 123) with lane-level accuracy. For example, a typical roadway lane is approximately 3 meters wide. However, a conventional GPS unit only has an accuracy of plus or minus 10 meters relative to the actual location of the ego vehicle 123. As a result, such conventional GPS units are not sufficiently accurate to enable the parking application 103 to determine the lane of travel of the ego vehicle 123. This measurement improves the accuracy of the GPS data describing the location of lanes used by the ego vehicle 123 when the parking application 103 is providing its functionality.

In some embodiments, the memory 127 stores two types of GPS data. The first is GPS data of the ego vehicle 123 and the second is GPS data of one or more objects (e.g., the remote vehicle 124 or some other object in the roadway environment). The GPS data of the ego vehicle 123 is digital data that describes a geographic location of the ego vehicle 123. The GPS data of the objects is digital data that describes a geographic location of an object. One or more of these two types of GPS data may have lane-level accuracy.

In some embodiments, one or more of these two types of GPS data are described by the sensor data 195. For example, the standard-compliant GPS unit 150 is a sensor included in the sensor set 126 and the GPS data is an example type of sensor data 195.

The communication unit 145 transmits and receives data to and from a network 105 or to another communication channel. In some embodiments, the communication unit 145 may include a DSRC transmitter, a DSRC receiver and other hardware or software necessary to make the ego vehicle 123 a DSRC-equipped device. For example, the communication unit 145 includes a DSRC antenna configured to broadcast DSRC messages via the network. The DSRC antenna may also transmit BSM messages at a fixed interval (e.g., every 0.1 seconds, at a time interval corresponding to a frequency range from 1.6 Hz to 10 Hz, etc.) that is user configurable. In some embodiments, the parking application 103 is operable to control all or some of the operation of the communication unit 145.

In some embodiments, the communication unit 145 includes a port for direct physical connection to the network 105 or to another communication channel. For example, the communication unit 145 includes a USB, SD, CAT-5, or similar port for wired communication with the network 105. In some embodiments, the communication unit 145 includes a wireless transceiver for exchanging data with the network 105 or other communication channels using one or more wireless communication methods, including: IEEE 802.11; IEEE 802.16, BLUETOOTH®; EN ISO 14906:2004 Electronic Fee Collection—Application interface EN 11253: 2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); EN 13372:2004 Dedicated Short-Range Communication (DSRC)—DSRC profiles for RTTT applications (review); the communication method described in U.S. patent application Ser. No. 14/471,387 filed on Aug. 28, 2014 and entitled "Full-Duplex Coordination System"; or another suitable wireless communication method.

In some embodiments, the communication unit 145 includes a full-duplex coordination system as described in U.S. Pat. No. 9,369,262 filed on Aug. 28, 2014 and entitled "Full-Duplex Coordination System," the entirety of which is incorporated herein by reference. In some embodiments, some, or all of the communications necessary to execute the methods described herein are executed using full-duplex wireless communication as described in U.S. Pat. No. 9,369,262.

In some embodiments, the communication unit 145 includes a cellular communications transceiver for sending and receiving data over a cellular communications network including via short messaging service (SMS), multimedia messaging service (MMS), hypertext transfer protocol (HTTP), direct data connection, WAP, e-mail, or another suitable type of electronic communication. In some embodiments, the communication unit 145 includes a wired port and a wireless transceiver. The communication unit 145 also provides other conventional connections to the network 105 for distribution of files or media objects using standard network protocols including TCP/IP, HTTP, HTTPS, and SMTP, millimeter wave, DSRC, etc.

In some embodiments, the communication unit 145 includes a V2X radio. The V2X radio is a hardware unit that includes one or more transmitters and one or more receivers that is operable to send and receive any type of V2X message. In some embodiments, the V2X radio is a C-V2X radio that is operable to send and receive C-V2X messages. In some embodiments, the C-V2X radio is operable to send and receive C-V2X messages on the upper 30 MHz of the 5.9 GHz band (i.e., 5.895-5.925 GHz). In some embodiments, some or all of the wireless messages described above with reference to the method 600 depicted in FIG. 6 or the method 700 depicted in FIG. 7 are transmitted by the C-V2X radio on the upper 30 MHz of the 5.9 GHz band (i.e., 5.895-5.925 GHz) as directed by the parking application 103.

In some embodiments, the V2X radio includes a DSRC transmitter and a DSRC receiver. The DSRC transmitter is operable to transmit and broadcast DSRC messages over the 5.9 GHz band. The DSRC receiver is operable to receive DSRC messages over the 5.9 GHz band. In some embodiments, the DSRC transmitter and the DSRC receiver operate on some other band which is reserved exclusively for DSRC.

In some embodiments, the V2X radio includes a non-transitory memory which stores digital data that controls the frequency for broadcasting BSMs. In some embodiments, the non-transitory memory stores a buffered version of the GPS data for the ego vehicle 123 so that the GPS data for the ego vehicle 123 is broadcast as an element of the BSM messages which are regularly broadcast by the V2X radio (e.g., at an interval of once every 0.10 seconds).

In some embodiments, the V2X radio includes any hardware or software which is necessary to make the ego vehicle 123 compliant with the DSRC standards. In some embodiments, the standard-compliant GPS unit 150 is an element of the V2X radio.

The memory 127 may include a non-transitory storage medium. The memory 127 may store instructions or data that may be executed by the processor 125. The instructions or data may include code for performing the techniques described herein. The memory 127 may be a dynamic random-access memory (DRAM) device, a static random-access memory (SRAM) device, flash memory, or some other memory device. In some embodiments, the memory 127 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

In some embodiments, the memory 127 may store any or all of the digital data or information described herein. As depicted in FIG. 1, the memory 127 stores the following digital data: the sensor data 195, training data 191, historical data 192, parking attribute data 193, and parking model data 196. The sensor data 195 was described above, and so, will not be described separately here as well.

The training data 191 includes digital data that is used to train a parking model based on a congestion level. In some embodiments, the training data 191 is used by the machine-learning module 204 described below with reference to FIG. 2 to train the parameters of parking model to generate different parking models based on a level of congestion of a parking facility.

The historical data 192 includes digital data that is used to personalize the parking models for a particular user. For example, the historical data 192 includes metadata about parking spots chosen by a user including, for example, historical geographical locations of vehicles and parking events, a time of day that the ego vehicle 123 parked in the parking spot, a length of time that the ego vehicle 123 parked in the parking spot, etc. The parking events include historical search paths that describe how a vehicle travelled to park in selected spots. In some embodiments, the historical data 192 is generated from the sensor data 195 recorded by the sensor set 126 that is particular to the historical search path, such as a location of the vehicle as a function of time.

In some embodiments, the historical data 192 includes GPS data that describes a geographic location of the ego vehicle 123, such as a longitude and latitude of the ego vehicle 123. In some embodiments, the vehicle GPS data may be retrieved by the DSRC-compliant GPS unit 150 of the ego vehicle 123 that is operable to provide GPS data describing the geographic location of the ego vehicle 123 with lane-level accuracy. Lane-level accuracy means that the location of the ego vehicle 123 is described by the GPS data so accurately that the lane of travel of the ego vehicle 123 within the roadway may be accurately determined based on the GPS data for this ego vehicle 123 as provided by the DSRC-compliant GPS unit 150.

The parking attribute data 193 includes digital data that describes attributes associated with parking facilities and parking spots. For example, the parking attribute data 193 associated with a parking facility includes: a number of available spots, a total number of parking spots, a number of electric vehicle (EV) charging stations, a number of available EV charging stations, geographical locations of the parking facility, geographical locations of parking entrances, geographical locations of points-of-interest around the parking facility, a parking fee, parking regulations, customer reviews, an average arrival rate of vehicles, an ease of parking indicator (for example, an average size of parking spots), and a recent history of availability. In another example, the parking attribute data 193 associated with parking spots include current availability, a recent history of availability, an estimated time when the parking spot becomes available, an average arrival rate of vehicles, whether the parking spot includes an EV charging station, whether the parking spot is handicapped parking, a distance from the parking spot to an entrance/doorway/exit, whether the parking spot is for a compact car, a dimension of the parking spot, a geographical location of the parking spot, a safety indicator (for example, a distance from closed captioning television (CCTV) cameras, a distance from a street light, etc.), and ease of parking indicators (for example, if the parking spot is located at a corner of a parking lot, traffic volume of an adjacent road segment, availability of adjacent spots, etc.).

The parking model data 196 includes digital data that is used to generate the different parking models. For example, the parking model data 196 may include digital data for generating a first parking model associated with a first congestion range, a second parking model associated with a second congestion range, and an nth parking model associated with an nth congestion range. In some embodiments, the parking application 103 receives an indication of a congestion level of a parking facility and identifies a corresponding parking model where the congestion level fits within a range for the corresponding parking model. The parking application 103 uses the corresponding parking model to identify a parking spot within the parking facility.

In some embodiments, the memory 127 stores some or all of the digital data described herein. In some embodiments, the memory 127 stores any digital data that is necessary for the parking application 103 to provide its functionality.

In some embodiments, the ego vehicle 123 includes a vehicle control system. A vehicle control system includes one or more ADAS systems or an autonomous driving system. Examples of an ADAS system include one or more of the following elements of a vehicle: an adaptive cruise control ("ACC") system; an adaptive high beam system; an adaptive light control system; an automatic parking system; an automotive night vision system; a blind spot monitor; a collision avoidance system; a crosswind stabilization system; a driver drowsiness detection system; a driver monitoring system; an emergency driver assistance system; a forward collision warning system; an intersection assistance system; an intelligent speed adaption system; a lane keep assistance ("LKA") system; a pedestrian protection system; a traffic sign recognition system; a turning assistant; and a wrong-way driving warning system. Other types of ADAS systems are possible. This list is illustrative and not exclusive.

An ADAS system is an onboard system of the ego vehicle 123 that is operable to identify one or more factors (e.g., using one or more onboard vehicle sensors) affecting the ego vehicle 123 and modify (or control) the operation of the ego vehicle to respond to these identified factors. Described generally, ADAS system functionality includes the process of (1) identifying one or more factors affecting the ego vehicle and (2) modifying the operation of the ego vehicle, or some component of the ego vehicle, based on these identified factors.

For example, an ACC system installed and operational in an ego vehicle may identify that a subject vehicle being followed by the ego vehicle with the cruise control system engaged has increased or decreased its speed. The ACC system may modify the speed of the ego vehicle based on the change in speed of the subject vehicle, and the detection of this change in speed and the modification of the speed of the ego vehicle is an example the ADAS system functionality of the ADAS system.

Similarly, an ego vehicle may have a LKA system installed and operational in an ego vehicle may detect, using one or more external cameras of the ego vehicle, an event in which the ego vehicle is near passing a center yellow line which indicates a division of one lane of travel from another lane of travel on a roadway. The LKA system may provide a notification to a user of the ego vehicle that this event has occurred (e.g., an audible noise or graphical display) or take action to prevent the ego vehicle from actually passing the center yellow line such as making the steering wheel difficult to turn in a direction that would move the ego vehicle over the center yellow line or actually moving the steering wheel so that the ego vehicle is further away from the center yellow line but still safely positioned in its lane of travel. The process of identifying the event and acting responsive to this event is an example of the ADAS system functionality provided by the LKA system.

The other ADAS systems described above each provide their own examples of ADAS system functionalities which are known in the art, and so, these examples of ADAS system functionality will not be repeated here.

In some embodiments, the ADAS system includes any software or hardware included in the vehicle that makes that vehicle be an autonomous vehicle or a semi-autonomous vehicle. In some embodiments, an autonomous driving system is a collection of ADAS systems which provides ADAS functionality to the ego vehicle 123 to render the ego vehicle 123 an autonomous or semi-autonomous vehicle.

An autonomous driving system includes a set of ADAS systems whose operation render autonomous functionality to render the ego vehicle 123 an autonomous vehicle (e.g., a Level III autonomous vehicle or higher as defined by the National Highway Traffic Safety Administration and the Society of Automotive Engineers).

In some embodiments, once the parking application 103 identifies a parking spot within the parking facility, the parking application 103 provides a recommendation to a user to select the parking spot. The user may select the parking spot and, as a result, the ADAS system automatically parks in the selected parking spot. In some embodiments, if the ego vehicle 123 is not autonomous (e.g., human driven), the parking application 103 generates a user interface that includes information about how to navigate to the available parking spot.

In some embodiments, the parking application 103 includes code and routines that are operable, when executed by the processor 125, to execute one or more steps of the method 500 described below with reference to FIG. 5 or one or more steps of the method 600 described below with reference to FIG. 6.

In some embodiments, the parking application 103 is an element of the onboard unit 139 or some other onboard vehicle computer. In some embodiments, the parking application 103 includes code and routines that are stored in the memory 127 and executed by the processor 125 or the onboard unit 139.

In some embodiments, the parking application 103 is implemented using hardware including a field-programmable gate array ("FPGA") or an application-specific integrated circuit ("ASIC"). In some other embodiments, the parking application 103 is implemented using a combination of hardware and software. The parking application 103 may be stored in a combination of the devices (e.g., servers or other devices), or in one of the devices. For example, the parking application 103B in the roadside unit 151 and/or the remote vehicle 124 may provide parking attribute data 193 to the parking application 103A in the ego vehicle 123, which uses the parking attribute data 193 to determine a parking spot in a parking facility.

The remote vehicles 124 may be any type of vehicle. For example, the remote vehicles 124 may include one of the following types of vehicles: a car; a truck; a sports utility vehicle; a bus; a semi-truck; a drone; or any other roadway-based conveyance. The remote vehicle 124 includes elements and functionality that are similar to those described above for the ego vehicle 123, and so, those descriptions will not be repeated here.

In some embodiments, the ego vehicle 123, the remote vehicle, and the roadside unit 151 are located in a roadway environment 140. For example, the roadway environment 140 could be the parking facility where the roadside unit 151 and the remote vehicle 124 provide the ego vehicle 123 with parking attribute data 193 to help the parking application 103 determine an available spot for the ego vehicle 123 that is consistent with the user's preferences.

The roadway environment 140 includes some or all of the tangible and/or measurable qualities described above with reference to the sensor data. In some embodiments, the real-world includes human experience comprising physical objects and excludes artificial environments and "virtual" worlds such as computer simulations.

In some embodiments, the roadside unit 151 includes an edge server 104. The edge server 104 is a connected processor-based computing device that includes an instance of the parking application 103 and a communication unit 145.

In some embodiments, the edge server 104 is one or more of the following: a hardware server; a personal computer; a roadside unit 151; or any other processor-based connected device that includes an instance of the parking application 103 and a non-transitory memory that stores some or all of the digital data that is stored by the memory 127 of the ego vehicle 123 or otherwise described herein. The edge server 104 may include a backbone network.

The edge server 104 includes an instance of the parking application 103. In some embodiments, the parking application 103 includes code and routines that are operable, when executed by the processor 125, to execute one or more steps of the method 500 described below with reference to FIG. 5 or the method 600 described below with reference to FIG. 6.

Example Computer System

Figure 2:
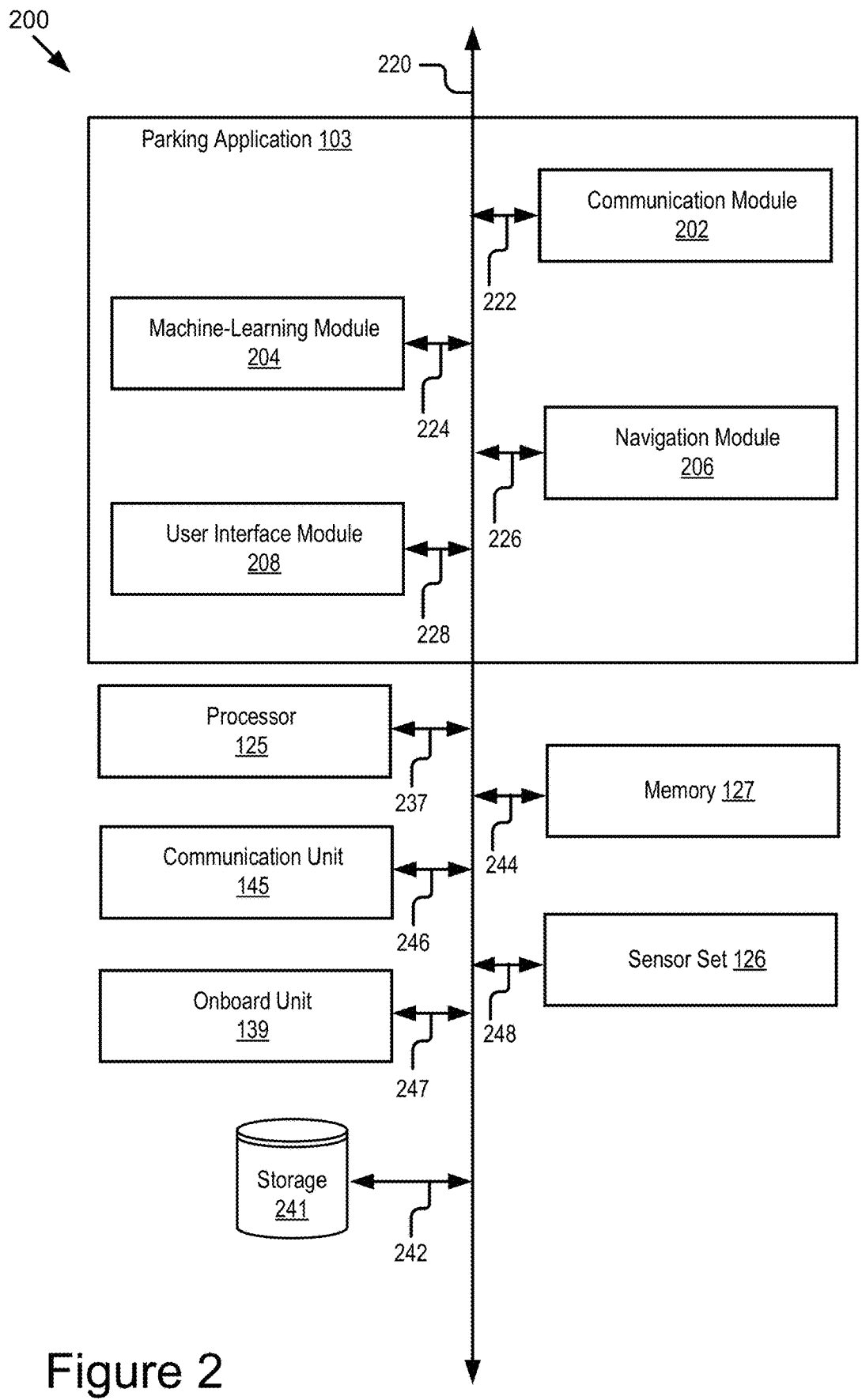
FIG. 2 is a block diagram illustrating an example computer system for a parking application according to some embodiments.

Referring now to FIG. 2, depicted is a block diagram illustrating an example computer system 200 including the parking application 103 according to some embodiments. In some embodiments, the computer system 200 may include a special-purpose computer system that is programmed to perform one or more steps of methods 500 and 600 described below with reference to FIGS. 5 and 6, respectively.

In some embodiments, the computer system 200 may be an element of a first connected device. For example, the first connected device can be the ego vehicle 123 or the edge server 104. The computer system 200 may be an element of the ego vehicle 123, an element of the edge server 104, or in part an element of the ego vehicle 123 and in part an element of the edge server 104.

The computer system 200 may include one or more of the following elements according to some examples: the parking application 103; the processor 125; the memory 127; the communication unit 145; the sensor set 126, the onboard unit 139; and a storage 241. The components of the computer system 200 are communicatively coupled by a bus 220. Although the computer system 200 is illustrated having the components of the ego vehicle 123, people of ordinary skill in the art will recognize that components may be added or removed depending on whether the computer system 200 is operating on the ego vehicle 123 or the edge server 104.

In the illustrated embodiment, the processor 125 is communicatively coupled to the bus 220 via a signal line 237. The memory 127 is communicatively coupled to the bus 220 via a signal line 244. The communication unit 145 is communicatively coupled to the bus 220 via a signal line 246. The sensor set 126 is communicatively coupled to the bus 220 via a signal line 248. The onboard unit 139 is communicatively coupled to the bus 220 via a signal line 247. The storage 241 is communicatively coupled to the bus 220 via a signal line 242.

The following elements of the computer system 200 are described above with reference to FIG. 1, and so, those descriptions will not be repeated here: the processor 125; the memory 127; the communication unit 145; the sensor set 126; and the onboard unit 139.

The memory 127 may store any of the data described above with reference to FIG. 1. The memory 127 may store any data necessary for the computer system 200 to provide its functionality.

The storage 241 can be a non-transitory storage medium that stores data for providing the functionality described herein. The storage 241 may be a dynamic random-access memory (DRAM) device, a static random-access memory (SRAM) device, flash memory, or some other memory devices. In some embodiments, the storage 241 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

In the illustrated embodiment shown in FIG. 2, the parking application 103 includes: a communication module 202; a machine-learning module 204; a navigation module 206; and a user interface module 208. These components of the parking application 103 are communicatively coupled to each other via the bus 220. In some embodiments, components of the parking application 103 can be stored in a single server or device. In some other embodiments, components of the parking application 103 can be distributed and stored across multiple servers or devices. For example, some of the components of the parking application 103 may be distributed across the edge server 104 and the ego vehicle 123.

The communication module 202 can be software including routines for handling communications between the parking application 103 and other components of the computer system 200. In some embodiments, the communication module 202 can be stored in the memory 127 of the computer system 200 and can be accessible and executable by the processor 125. The communication module 202 may be adapted for cooperation and communication with the processor 125 and other components of the computer system 200 via a signal line 222.

The communication module 202 sends and receives data, via the communication unit 145, to and from one or more elements of the operating environment 100. For example, the communication module 202 receives parking attribute data 193 from the communication unit 145 that is part of the roadside unit 151. The communication module 202 may send or receive any of the data or messages described above with reference to FIG. 1 via the communication unit 145. In another example, where a parking application 103A is stored on the ego vehicle 123, but the parking application 103B that is part of the roadside unit 151 determines a parking model based on a congestion level, the communication module 202 provides sensor data 195 to the parking application 103 that is part of the roadside unit 151.

In some embodiments, the communication module 202 receives data from components of the parking application 103 and stores the data in one or more of the storage 241 and the memory 127. For example, the communication module 202 receives any of the data described above with reference to the memory 127 from the communication unit 145 (via the network 105, a DSRC message, a BSM, a DSRC probe, a full-duplex wireless message, etc.) and stores this data in the memory 127 (or temporarily in the storage 241 which may act as a buffer for the computer system 200). In another example, the communication module 202 receives sensor data 195 from the sensor set 126 and stores the sensor data in the memory 127.

In some embodiments, the communication module 202 may handle communications between components of the parking application 103. For example, the communication module 202 may handle communications among the machine-learning module 204 and the user interface module 208. Any of these modules may cause the communication module 202 to communicate with the other elements of the computer system 200 or the operating environment 100 (via the communication unit 145).

The machine-learning module 204 can be software including routines for generating multiple parking levels with different congestion ranges. In some embodiments, the machine-learning module 204 can be stored in the memory 127 of the computer system 200 and can be accessible and executable by the processor 125. The machine-learning module 204 may be adapted for cooperation and communication with the processor 125 and other components of the computer system 200 via a signal line 224.

In some embodiments, the machine-learning module 204 receives training data 191 that includes historical data of paths of different drivers for a set of vehicles and how they correspond to different congestion levels. For example, the machine-learning module 204 may receive training data 191 that describes the movement of a set of vehicles in a geographic location over a time period, the locations of all parking spots in the geographic location, and the corresponding congestion levels. The machine-learning module 204 may compare the movement of the set of vehicles with the location of the parking spots and the congestion level to identify behavior of the set of vehicles, such as when and where vehicles in the set of vehicles parked in the parking spots as a function of a level of congestion of the parking facility. The comparison may reveal information about preference, such as that some drivers may be more willing to park farther away from an exit when there is a high level of congestion in a parking facility because the drivers may be more willing to walk longer distances in exchange for not having to drive around to find a spot that is closest to the exit.

The machine-learning module may modify the parameters of a parking model based on the training data 191. In some embodiments, the training data is supervised. The training data 191 may include supervised training data where the historical data of paths of different drivers are identified as being associated with particular congestion levels. The training data 191 may include unsupervised training data where the historical paths of different drivers are not identified as being associated with particular congestion levels, but the machine-learning module 204 is able to discern that different behaviors are associated with different congestion levels.

In some embodiments, the machine-learning module 204 uses the training data 191 to generate multiple parking models that correspond to different congestion ranges. For example, the machine-learning module 204 may generate a first parking model that is associated with a first congestion range and a second parking model that is associated with a second congestion range. The congestion ranges may be based on the preference of the drivers associated with the training data 191. The machine-learning module 204 may update the parking models responsive to receiving historical data 192 that is particular to a user associated with the ego vehicle 123.

In some embodiments, the machine-learning module 204 receives historical data 192 that describes how the ego vehicle 123 travelled to park in selected spots and locations of other available parking spots in parking facilities and corresponding congestion levels associated with the parking facilities. In some embodiments, the historical data 192 is the training data 191 and the machine-learning module 204 generates the parking models based on the historical data 192. In some embodiments, the machine-learning module 204 generates the parking models using the training data 191 associated with other drivers and updates the parameters of the parking models after receiving the historical data 192 in order to personalize the parking models for the user of the ego vehicle 123. The machine-learning module 204 saves the parking models as parking model data 196.

In some embodiments, the machine-learning module 204 uses the historical data 192 to detect available parking spots along a historical search path and determines that the parking spot selected by the ego vehicle 123 is the parking spot preferred by the user. For each parking event, which is described by the historical search path, the machine-learning module 204 calculates a per-criterion score $f_j(s_i)$ of each available parking spot $s_i$ along a candidate search path. The machine-learning module 204 trains a parking model $f_j$ to score different available parking spots and associates the parking model with a congestion range. The congestion range may be a predefined system parameter or the congestion range may be determined by the machine-learning module 204 based on the historical data 192. In some embodiments, the machine-learning module 204 uses the historical data 192 to detect both available parking spots and available parking facilities along a historical path and trains the parking model based on parking facilities and parking spots.

Figure 3:
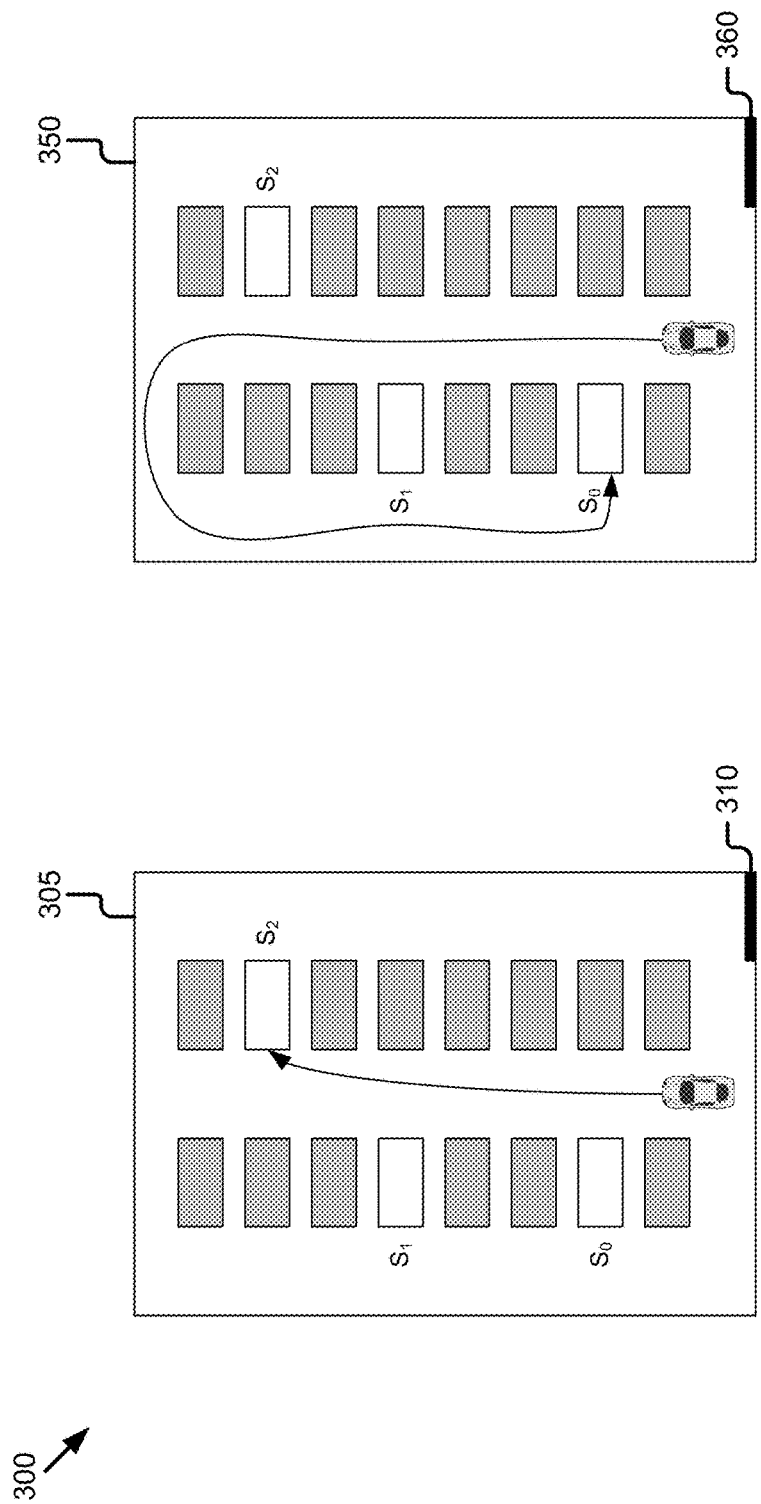
FIG. 3 is an example block diagram illustrating different parking events with different congestion levels according to some embodiments.

Turning to FIG. 3, an example block diagram 300 illustrates different parking events with different congestion levels that are used as historical data 192. In the first example 305, there are three available parking spots: $S_0$, $S_1$, and $S_2$. $S_0$ is closest to the exit 310. In the first example 305, the machine-learning module 204 trains the parking model so that $f_j(s_0) < f_j(s_2)$ and $f_j(s_1) < f_j(s_2)$. In this example, the congestion range is 20/100 to 25/100.

In the second example 350, there are three available parking spots: $S_0$, $S_1$, and $S_2$. So is closest to the exit 360. In the second example 350, the machine-learning module 204 trains the parking model so that $f_j(s_2) < f_j(s_0)$ and $f_j(s_1) < f_3(s_0)$. In this example, the congestion range is 0/100 to 5/100.

In the first example 305, the ego vehicle 123 took the closest parking spot that was available. In the second example 350, the ego vehicle 123 drove past two available parking spots in order to reach the parking spot that was closest to the exit 360. It is possible to infer from comparison of the two examples that the ego vehicle 123 is willing to take the closest space when the parking facility has a higher congestion rate than when the parking facility has a lower congestion rate.

The machine-learning module 204 may generate a parking model with a variety of model forms or structures, such as a linear regression model, a neural-network (e.g., a convolutional neural network, a linear network), a deep neural network that implements a plurality of layers (e.g., hidden layers between an input layer and an output layer, with each layer being a linear network), a convolutional neural network (e.g., a network that splits or partitions input data into multiple parts or tiles, processes each tile separately using one or more neural-network layers, and aggregates the results from the processing of each tile), a sequence-to-sequence neural network (e.g., a network that takes as input sequential data such as a series of locations of a vehicle, images of a parking lot, etc. and produces as output a result sequence), etc.

Once the machine-learning module 204 generates multiple parking models, the machine-learning module 204 may receive a current search path, at least one parking facility that is within proximity to the ego vehicle 123 along the search path along with candidate parking spots, and a corresponding congestion level for the at least one parking facility. In some embodiments, the machine-learning module 204 receives an identification of the candidate parking spots that are available within the at least one parking facility from onboard sensors of remote vehicles 124 travelling within the parking facility. In some embodiments, the machine-learning module 204 receives candidate parking spots from one or more roadside units 151. In some embodiments, the machine-learning module 204 receives video streams from surveillance cameras in the parking facility and determines an availability of candidate parking spots based on applying an image processing algorithm to the video streams, receives data from roadway occupancy sensors in a roadside unit 151 that detect a presence of vehicles in occupied parking spots, or other techniques for identifying candidate parking spots known to those of ordinary skill in the arts. In some embodiments, the machine-learning module 204 receives the search path from a navigation module 206 that determines a navigation trip and an end of the navigation trip.

The machine-learning module 204 may determine a parking model to apply based on the congestion level and the current search path provided as input to the parking model. The parking model may output scores for candidate parking facilities and scores for the candidate parking spots within each of the candidate parking facilities.

In some embodiments, the training data 191 includes other parking attributes besides the availability of parking spots in parking facilities and the machine-learning module 204 generates the parking models based on the other parking attributes. For example, the training data 191 may include a sports utility vehicle (SUV) with particular dimensions and information about how the vehicle selects only parking spots with dimensions greater than the dimensions of the vehicle. Conversely, the training data 191 may include a compact vehicle that parks in both spots designed for compact cars and other parking spots.

In some embodiments, when the machine-learning module 204 uses historical data 192 related to the ego vehicle 123 to personalize the parking models, the machine-learning module 204 also receives parking attribute data 193 that describes other parking attributes associated with a parking facility and/or parking spot that the ego vehicle 123 parked in. For example, the machine-learning module 204 uses a distance from a parking spot that the ego vehicle 123 used to an exit to determine a user's preference for parking close to an exit. In another example, the parking attribute data 193 may include information about lighting conditions surrounding candidate parking spots and the parking model scores a candidate parking spot based on user preferences about parking in well lit areas, especially went the ego vehicle 123 is parking after sunset. The machine-learning module 204 may determine user preferences for parking attributes by comparing the historical data 192 of historical search paths to parking attribute data 193 that describes the parking attributes of each parking spot.

The machine-learning module 204 identifies a parking spot for the vehicle within the parking facility based on a selected parking model. For example, the machine-learning module 204 selects a first parking model that scores candidate parking spots that are available within a parking facility, ranks the candidate parking spots, and generates a recommendation for the parking spot along a parking search based on the parking spot having a best ranking. In some embodiments, the machine-learning module 204 instructs the user interface module 208 to generate a user interface that includes a search path to reach the parking spot.

In some embodiments, the machine-learning module 204 updates the parking models based on feedback. The user interface module 208 may provide a recommendation to the user of the ego vehicle 123. For example, the user interface module 208 displays a user interface with a recommendation to park along with a corresponding map. In some embodiments, the machine-learning module 204 receives feedback from the user of the ego vehicle 123 about the recommendation either because the user selected the recommendation or rejected the recommendation. The machine-learning module 204 updates the corresponding parking model based on the feedback. For example, if the user selects a recommendation generated by a first parking model, the machine-learning module 204 updates the parameters of the first parking model to generate similar recommendations in the future. Conversely, if the user rejects the recommendation generated by the first parking model, the machine-learning module 204 updates the parameters to avoid a similar recommendation in the future. If the user rejects the recommendation, the machine-learning module 204 may determine, for example, that the congestion range associated with the first parking model needs to be modified.

The navigation module 206 can be software including routines for generating a request that describes a need for the ego vehicle 123 to park. In some embodiments, the navigation module 206 can be stored in the memory 127 of the computer system 200 and can be accessible and executable by the processor 125. The navigation module 206 may be adapted for cooperation and communication with the processor 125 and other components of the computer system 200 via a signal line 226.

The navigation module 206 may provide navigation services to a driver of the ego vehicle 123. For example, the driver may input a travel destination into a user interface generated by the user interface module 208. The navigation module 206 may generate driving directions that the user interface displays to help navigate the user to the travel destination. In some embodiments, the navigation module 206 may determine the travel destination based on historical travel data. For example, the navigation module 206 may determine that the driver is going to work based on driving to work starting at 8:45 every Monday through Friday.

In some embodiments, the navigation module 206 may determine that the ego vehicle 123 is within a threshold distance of the travel destination and, responsive to determining that the ego vehicle 123 is within the threshold distance, generate a request that describes a need for the ego vehicle to park. The navigation module 206 may instruct the communication unit 145 to transmit the request to the machine-learning module 204 on the ego vehicle 123.

The navigation module 206 receives the geographic location of a parking spot from the machine-learning module 204. In embodiments where the ego vehicle 123 includes an ADAS system and the user selected the recommendation to park in the parking spot, the navigation module 206 instructs the ADAS system via the communication unit 145 to automatically park in the available parking spot. In embodiments where the ego vehicle 123 does not include the ADAS system, the navigation module 206 instructs the user interface module 208 to update the user interface to include the geographic location of the available parking spot and instructions for how to navigate to the parking spot.

The navigation module 206 may continue to send instructions to the user interface module 208 to update the user interface to help guide the driver to find the available parking spot. In some embodiments, the computer system 200 includes speakers and the navigation module 206 instructs the speakers to provide additional instructions to help the driver find the available parking spot. This advantageously improves the safety of the ego vehicle 123 by preventing the driver from having to stare at a user interface that fails to help the driver locate the available parking spot.

The user interface module 208 can be software including routines for generating a user interface. In some embodiments, the user interface module 208 can be stored in the memory 127 of the computer system 200 and can be accessible and executable by the processor 125. The user interface module 208 may be adapted for cooperation and communication with the processor 125 and other components of the computer system 200 via a signal line 228.

The user interface module 208 generates graphical data for displaying a user interface on a display. The display may be hardware that is part of the ego vehicle 123, such as a touchscreen display that is located in the center console, a heads-up display unit, or any other type of display that is inside the ego vehicle 123. The display may also be part of a mobile device that is associated with a user, such as the driver or a passenger of the ego vehicle 123.

Figure 4:
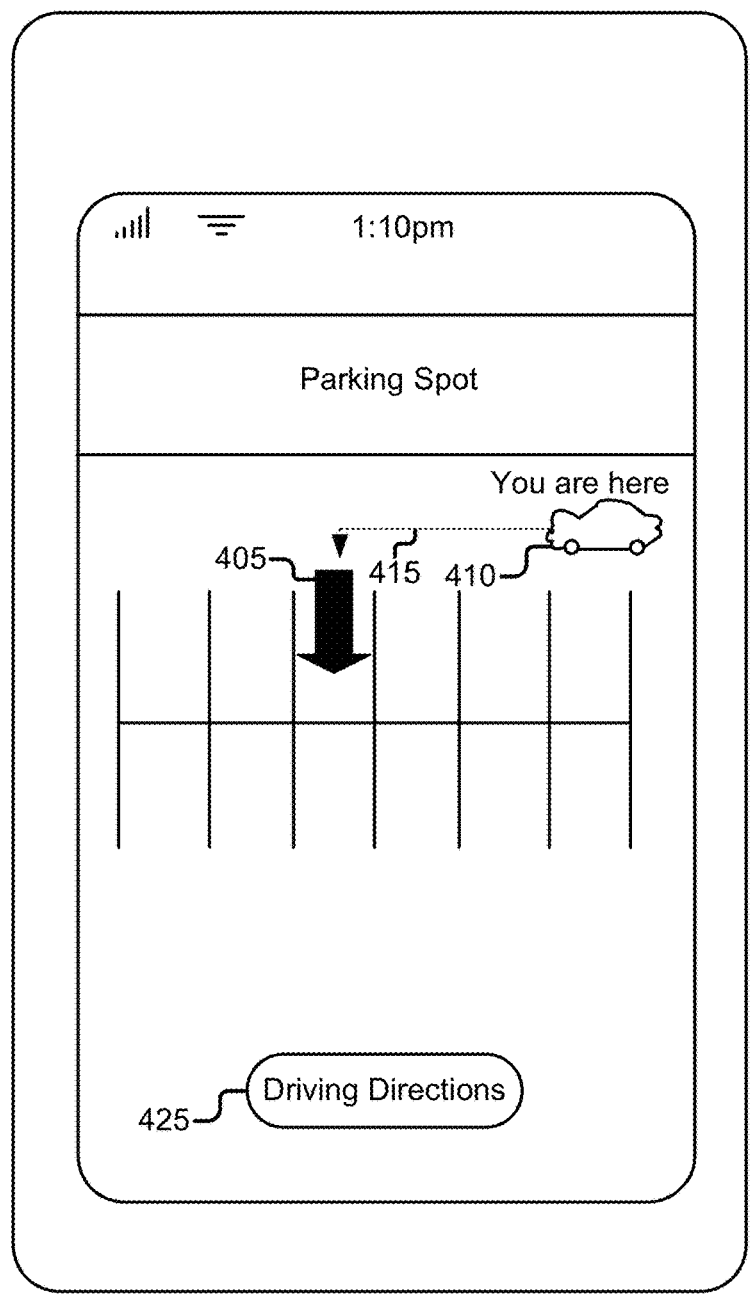
FIG. 4 is an example user interface illustrating a parking spot along a search path according to some embodiments.

Turning to FIG. 4, an example user interface 400 of a parking spot along a search path is illustrated. In this example, the user interface module 208 generated graphical data to display the parking spot as indicated by the solid arrow 405. The user interface also includes an icon 410 of the driver's car with the following indicator "You are here" and a dashed arrow 415 that traces a search path from the current location of the car to the available parking spot. Lastly, the user interface 400 includes a selectable button 425 for returning to a "Driving Directions" page that displays information about navigating from an initial destination to the travel destination.

The user interface module 208 may update the user interface as the ego vehicle 123 moves to show how the ego vehicle 123 is moving relative to the available parking spot. The user interface module 208 may also update the estimated length of availability as time passes. For example, the estimated length of availability may decrease per second and once the estimated length of availability falls below a threshold time (such as 30 seconds) the estimated length of availability may change to indicate that a change is imminent, such as by changing from black to red text.

In some embodiments, the user interface module 208 generates a user interface that allows a user to configure different settings. For example, the user may be able to specify the congestion range for different parking models. In some embodiments, if a user does not adapt a recommendation for a parking spot, the user interface may include a request for feedback to improve the process. For example, the request for feedback may include radio buttons with reasons why the user rejected the recommendation, such as "too far from the exit," "too worried that the spot might be taken," "the spot was too small," etc. In another example, the request for feedback includes a field that allows a user to input a more specific reason about why the user rejected the recommendation.

Example Processes

Figure 5:
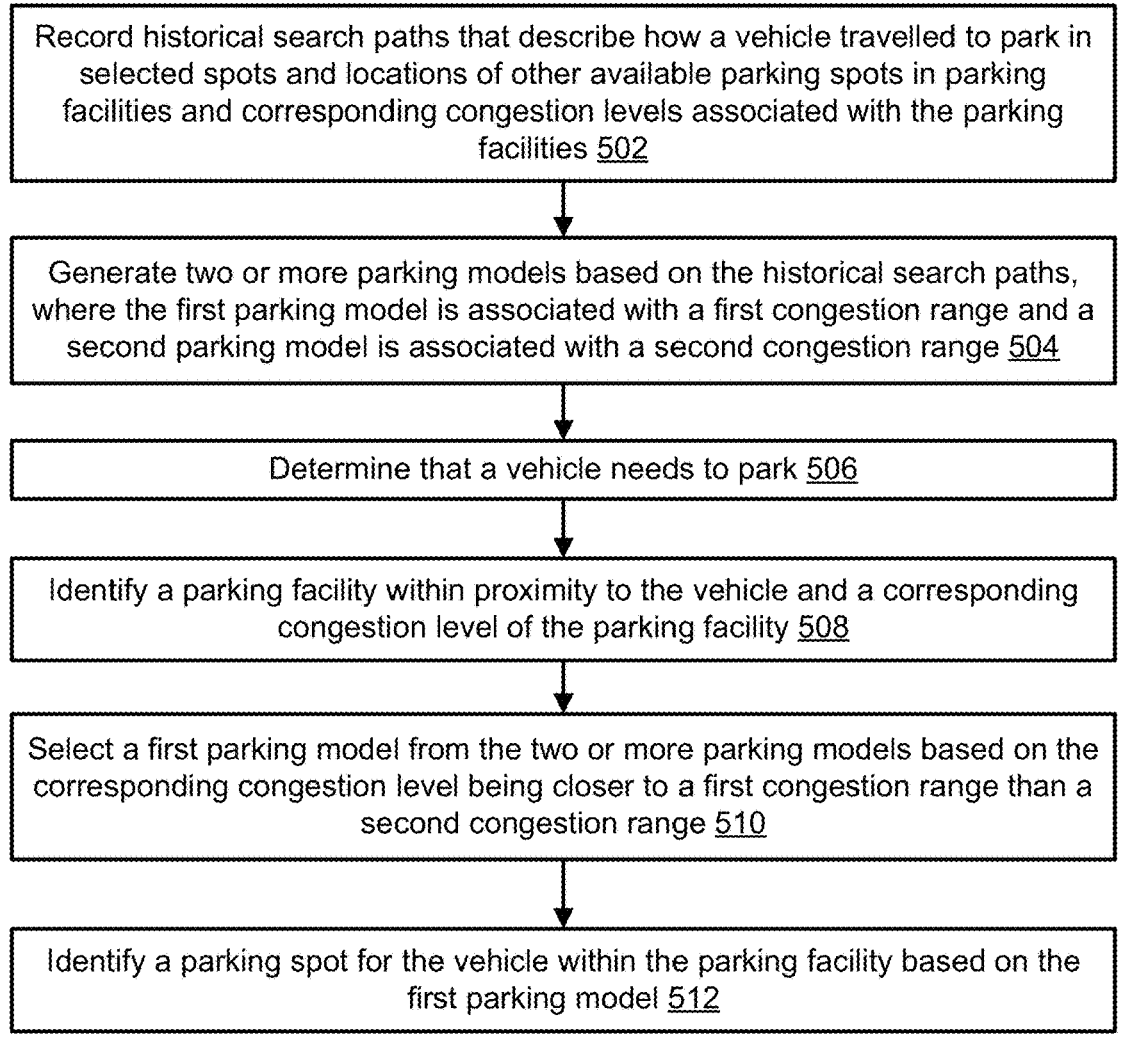
FIG. 5 depicts a flowchart of an example method for identifying a parking spot according to some embodiments.

Referring now to FIG. 5, depicted is a flowchart of an example method 500 for identifying a parking spot according to some embodiments. The steps of the method 500 are executable in any order, and not necessarily the order depicted in FIG. 5. In some embodiments, the method 500 is performed by the parking application 103A stored on the ego vehicle 123. In some embodiments, the method 500 is performed by the parking application 103B stored on the roadside unit 151. In some embodiments, part of the method 500 is performed by the parking application 103A stored on the ego vehicle 123 and part of the method 500 is performed by the parking application 103B stored on the roadside unit.

At step 502, historical search paths are recorded that describe how a vehicle travelled to park in selected spots and locations of other available parking spots in parking facilities and corresponding congestion levels associated with the parking facilities. For example, the historical search paths are part of the historical data 192 recorded by the sensor set 126 of the ego vehicle.

At step 504, two or more parking models are generated based on the historical search paths, where the first parking model is associated with a first congestion range and a second parking model is associated with a second congestion range. The parking models may be machine-learning models.

At step 506, it is determined that a vehicle needs to park. For example, the navigation module 206 may determine that the ego vehicle 123 is nearing an end of a navigation trip.

At step 508, a parking facility within proximity to the vehicle and a corresponding congestion level of the parking facility are determined. For example, the parking facility may be within proximity to the vehicle at the end of the navigation trip.

At step 510, a first parking model is selected from the two or more parking models based on the corresponding congestion level being closer to a first congestion range than a second congestion range. For example, the corresponding congestion level may be 4/100 parking spots are available, the first congestion range is 0-4/100 parking spots are available, and the second congestion range is 55-60/100 parking spots are available.

At step 512, a parking spot is identified for the vehicle within the parking facility based on the first parking model. In some embodiments, the first parking model scores each candidate parking spots and ranks the candidate parking spots based on the scores. In some embodiments, the first parking model also uses parking attribute data 193 to score the candidate parking spots. For example, the first parking model may give a more favorable score to candidate parking spots that have EV charging stations as indicated by the parking attribute data 193 based on the historical data 192 for the ego vehicle 123 indicating that the user is more likely to select parking spots with EV charging stations.

Figure 6:
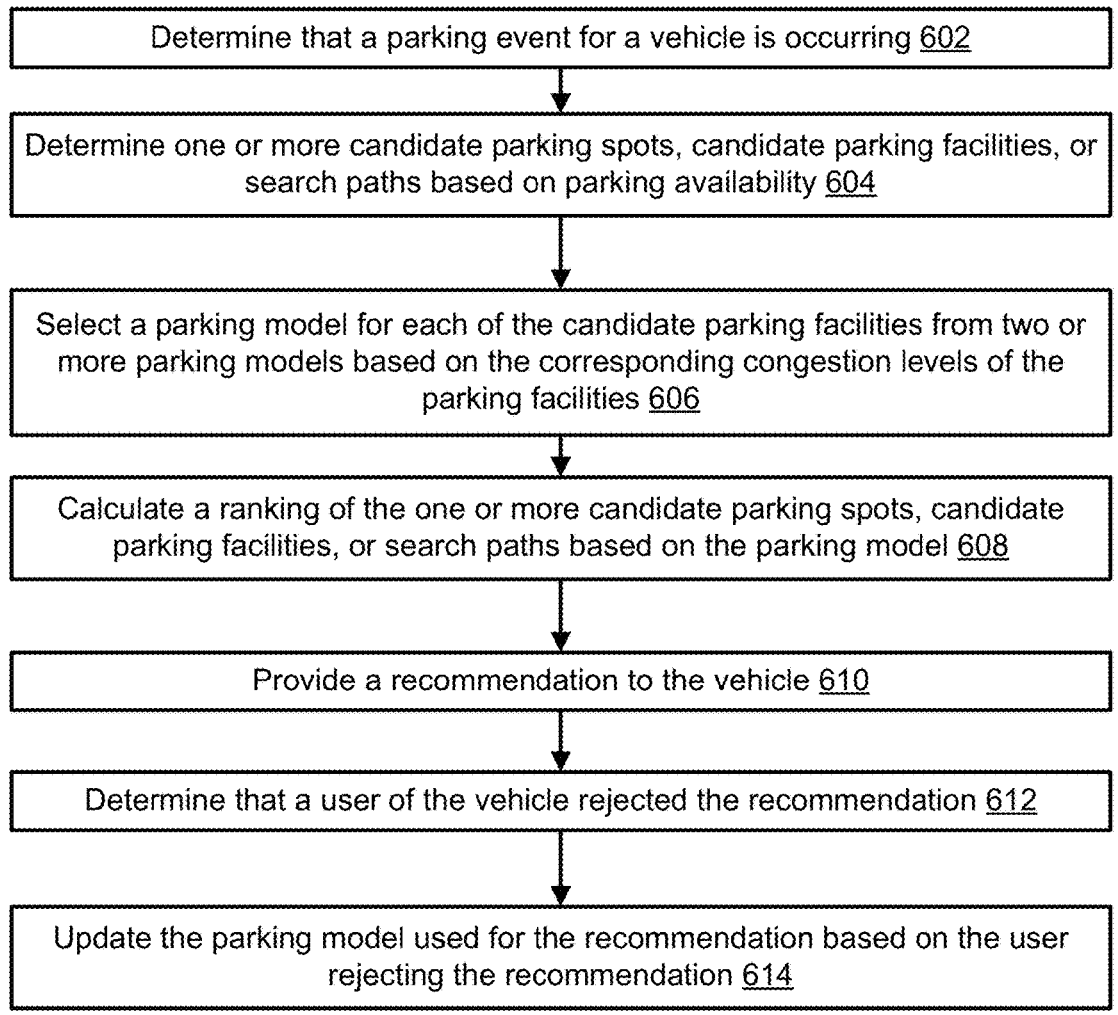
FIG. 6 depicts a flowchart of another example method for identifying a parking spot according to some embodiments.

Referring now to FIG. 6, depicted is a flowchart of another example method 600 for identifying a parking spot according to some embodiments. The steps of the method 600 are executable in any order, and not necessarily the order depicted in FIG. 6. In some embodiments, the method 600 is performed by the parking application 103A stored on the ego vehicle 123. In some embodiments, the method 600 is performed by the parking application 103B stored on the roadside unit 151. In some embodiments, part of the method 600 is performed by the parking application 103A stored on the ego vehicle 123 and part of the method 600 is performed by the parking application 103B stored on the roadside unit.

At step 602, a parking event for a vehicle is determined. For example, a parking event may be a past occurrence of a location where a vehicle parked.

At step 604, one or more candidate parking spots, candidate parking facilities, or search paths are determined based on parking availability. In some embodiments, a segment of the vehicle's historical trajectory is used to define the search paths. For example, a start of a search path is a location of the vehicle when it starts to search for parking and an end of the search path is a location where a parking event was detected.

At step 606, a parking model is selected for each of the candidate parking facilities from two or more parking models based on the corresponding congestion levels of the parking facilities.

At step 608, a ranking of one or more candidate parking spots, candidate parking facilities, or search paths is calculated based on the parking model.

At step 610, a recommendation is provided to the vehicle.

At step 612, a user of the vehicle is determined to have rejected the recommendation.

At step 614, the parking model used for the recommendation is updated based on the user rejecting the recommendation.

In the above description, for purposes of explanation, numerous specific details are set forth in order to provide a thorough understanding of the specification. It will be apparent, however, to one skilled in the art that the disclosure can be practiced without these specific details. In some instances, structures and devices are shown in block diagram form in order to avoid obscuring the description. For example, the present embodiments can be described above primarily with reference to user interfaces and particular hardware. However, the present embodiments can apply to any type of computer system that can receive data and commands, and any peripheral devices providing services.

Reference in the specification to "some embodiments" or "some instances" means that a particular feature, structure, or characteristic described in connection with the embodiments or instances can be included in at least one embodiment of the description. The appearances of the phrase "in some embodiments" in various places in the specification are not necessarily all referring to the same embodiments.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The present embodiments of the specification can also relate to an apparatus for performing the operations herein. This apparatus may be specially constructed for the required purposes, or it may include a general-purpose computer selectively activated or reconfigured by a computer program stored in the computer. Such a computer program may be stored in a computer-readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory, or any type of media suitable for storing electronic instructions, each coupled to a computer system bus.

The specification can take the form of some entirely hardware embodiments, some entirely software embodiments or some embodiments containing both hardware and software elements. In some preferred embodiments, the specification is implemented in software, which includes, but is not limited to, firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A data processing system suitable for storing or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including, but not limited, to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem, and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the embodiments of the specification has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions, or formats. Furthermore, as will be apparent to one of ordinary skill in the relevant art, the modules, routines, features, attributes, methodologies, and other aspects of the disclosure can be implemented as software, hardware, firmware, or any combination of the three. Also, wherever a component, an example of which is a module, of the specification is implemented as software, the component can be implemented as a standalone program, as part of a larger program, as a plurality of separate programs, as a statically or dynamically linked library, as a kernel-loadable module, as a device driver, or in every and any other way known now or in the future to those of ordinary skill in the art of computer programming. Additionally, the disclosure is in no way limited to embodiment in any specific programming language, or for any specific operating system or environment. Accordingly, the disclosure is intended to be illustrative, but not limiting, of the scope of the specification, which is set forth in the following claims.

What is claimed is:

1. A method comprising:
   determining that a vehicle needs to park;
   identifying a parking facility within proximity to the vehicle and a corresponding congestion level of the parking facility;
   selecting a first parking model from two or more parking models based on the corresponding congestion level being closer to a first congestion range than a second congestion range; and
   identifying a parking spot for the vehicle within the parking facility based on the first parking model.

2. The method of claim 1, further comprising:
   recording historical search paths that describe how the vehicle travelled to park in selected spots and locations of other available parking spots in the parking facilities and the corresponding congestion levels associated with the parking facilities; and
   generating the two or more parking models based on the historical search paths, wherein the first parking model is associated with the first congestion range and a second parking model is associated with the second congestion range.

3. The method of claim 2, wherein identifying the parking spot for the vehicle within the parking facility includes:
   receiving an identification of candidate parking spots that are available within the parking facility, wherein the candidate parking spots are identified based on onboard sensors of vehicles travelling within the parking facility;
   scoring the candidate parking spots within the parking facility based on the first parking model, wherein the first parking model uses parking attributes to score the candidate parking spots; and
   generating a recommendation for the parking spot along a parking search path based on the parking spot having a best ranking.

4. The method of claim 3, wherein scoring the candidate parking spots includes calculating a per-criterion score for each candidate parking spot along a candidate search path and the corresponding congestion levels are defined as a ratio of available parking spots to occupied parking spots.

5. The method of claim 2, wherein the two or more parking models are generated by a machine-learning model and training data for the machine-learning model includes historical search paths for a set of vehicles.

6. The method of claim 1, further comprising:
   providing a recommendation to a user of the vehicle with the parking spot;
   receiving a selection from the user of the parking spot that was identified; and
   instructing an autonomous vehicle system of the vehicle to automatically park in the parking spot.

7. The method of claim 1, further comprising:
   providing a recommendation to a user of the vehicle with the parking spot;

determining that the user rejected the recommendation of the parking spot; and updating the first parking model based on the user rejecting the recommendation.

8. The method of claim 1, further comprising displaying a recommendation for the parking spot within a user interface, wherein the recommendation includes a search path to reach the parking spot.

9. The method of claim 1, wherein determining that the vehicle needs to park is based on identifying a navigation trip and wherein identifying the parking facility within proximity to the vehicle includes identifying the parking facility within proximity to the vehicle at an end of the navigation trip.

10. A system for an ego vehicle, comprising:
a processor; and
a non-transitory memory storing computer code which, when executed by the processor, causes the processor to:
determine that a vehicle needs to park;
identify a parking facility within proximity to the vehicle and a corresponding congestion level of the parking facility;
select a first parking model from two or more parking models based on the corresponding congestion level being closer to a first congestion range than a second congestion range; and
identify a parking spot for the vehicle within the parking facility based on the first parking model.

11. The system of claim 10, wherein the computer code, when executed by the processor, further causes the processor to:
record historical search paths that describe how the vehicle travelled to park in selected spots and locations of other available parking spots in the parking facilities and the corresponding congestion levels associated with the parking facilities; and
generate the two or more parking models based on the historical search paths, wherein the first parking model is associated with the first congestion range and a second parking model is associated with the second congestion range.

12. The system of claim 11, wherein identifying the parking spot for the vehicle within the parking facility includes:
receiving an identification of candidate parking spots that are available within the parking facility, wherein the candidate parking spots are identified based onboard sensors of vehicles travelling within the parking facility;
scoring the candidate parking spots within the parking facility based on the first parking model, wherein the first parking model uses parking attributes to score the candidate parking spots; and
generating a recommendation for the parking spot along a parking search path based on the parking spot having a best ranking.

13. The system of claim 12, wherein scoring the candidate parking spots includes calculating a per-criterion score for each candidate parking spot along a candidate search path and the corresponding congestion levels are defined as a ratio of available parking spots to occupied parking spots.

14. The system of claim 11, wherein the two or more parking models are generated by a machine-learning model and training data for the machine-learning model includes historical search paths for a set of vehicles.

15. A computer program product comprising a non-transitory memory storing computer-executable code that, when executed by a processor, causes the processor to:
determine that a vehicle needs to park;
identify a parking facility within proximity to the vehicle and a corresponding congestion level of the parking facility;
select a first parking model from two or more parking models based on the corresponding congestion level being closer to a first congestion range than a second congestion range; and
identify a parking spot for the vehicle within the parking facility based on the first parking model.

16. The computer program product of claim 15, wherein the computer code, when executed by the processor, further causes the processor to:
record historical search paths that describe how the vehicle travelled to park in selected spots and locations of other available parking spots in the parking facilities and the corresponding congestion levels associated with the parking facilities; and
generate the two or more parking models based on the historical search paths, wherein the first parking model is associated with the first congestion range and a second parking model is associated with the second congestion range.

17. The computer program product of claim 16, wherein identifying the parking spot for the vehicle within the parking facility includes:
receiving an identification of candidate parking spots that are available within the parking facility, wherein the candidate parking spots are identified based on onboard sensors of vehicles travelling within the parking facility;
scoring the candidate parking spots within the parking facility based on the first parking model, wherein the first parking model uses parking attributes to score the candidate parking spots; and
generating a recommendation for the parking spot along a parking search path based on the parking spot having a best ranking.

18. The computer program product of claim 17, wherein scoring the candidate parking spots includes calculating a per-criterion score for each candidate parking spot along a candidate search path and the corresponding congestion levels are defined as a ratio of available parking spots to occupied parking spots.

19. The computer program product of claim 16, wherein the two or more parking models are generated by a machine-learning model and training data for the machine-learning model includes historical search paths for a set of vehicles.

20. The computer program product of claim 15, wherein identifying the parking spot for the vehicle within the parking facility includes:
providing a recommendation to a user of the vehicle with the parking spot;
receiving a selection from the user of the parking spot that was identified; and
instructing an autonomous vehicle system of the vehicle to automatically park in the parking spot.

* * * * *